Aug. 30, 1955 E. S. BOERNER Plant Pat. 1,415
ROSE PLANT
Filed Nov. 5, 1954
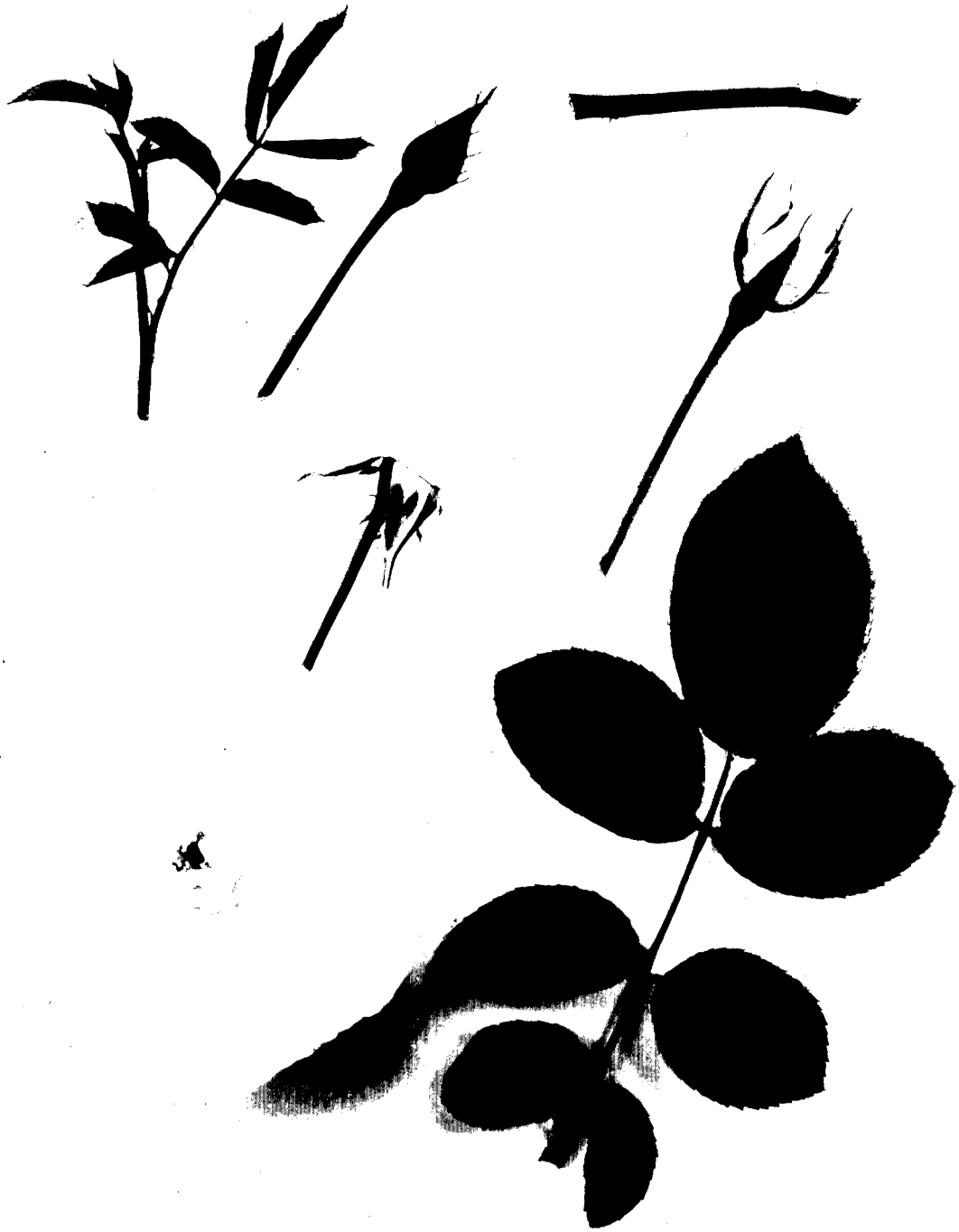
Inventor.
E. S. Boerner
By: Robb & Robb
Attorneys.

United States Patent Office

Plant Pat. 1,415
Patented Aug. 30, 1955

1,415

ROSE PLANT

Eugene S. Boerner, Newark, N. Y., assignor to Jackson & Perkins Company, Newark, N. Y., a corporation of New York Application November 5, 1954, Serial No. 467,249

1 Claim. (Cl. 47—61)

The present invention relates to a new and distinct variety of rose plant of the large-flowered polyantha class, which was originated by me by crossing the variety "Glacier" (Plant Patent No. 1,025) with an unnamed and unpatented seedling of "Pinocchio" (Plant Patent No. 484).

The primary objective in making this cross was to produce a new variety of rose plant which bears white flowers and which is more vigorous than the parent variety "Glacier," while at the same time, obtaining a white-flowered variety which is suitable for greenhouse growing for the production of cut flowers, which is something much needed in the class of White Floribundas. These objectives were fully achieved by crossing the variety "Glacier" with a seedling that is characterized by its great vigor and freedom of growth, with the result that the new variety is particularly characterized by its vigorous, free-growing and free-production habits under normal greenhouse conditions, which makes it very suitable for cut flower production, by the attractive shape of its half-open buds which are very adaptable for cut flowers, by the flat shape of its open flowers, resulting in almost hiding the stamens, which is a very interesting and different characteristic, and by the white color of its flowers comparable to the color of "Glacier."

The foregoing characteristics definitely differentiate my new variety from its parents, as well as from all other varieties of which I am aware, and asexual reproduction of the new variety by budding at Newark, New York, and also at Pleasanton, California, shows that the foregoing characteristics and distinctions come true to form and are established and transmitted through succeeding propagations.

The accompanying drawing shows typical specimens of the foliage, stems and flowers of my new variety in different stages of development, and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
- *Seed parent.*—"Glacier."
- *Pollen parent.*—An unnamed seedling of "Pinocchio."

Classification:
- *Botanic.*—Large-flowered polyantha.
- *Commercial.*—Floribunda.

FLOWER (Observations made in a greenhouse at Newark, New York, in the month of March and in the mid-afternoon.)

Blooming habit: Recurrent—Continuous; very free greenhouse flowering variety, producing many flowers.

Bud:
- *Size.*—Medium.
- *Form.*—Ovoid; is not affected by wet or hot weather.

- *Color.*—When sepals first divide—Light Dull Green-Yellow, Plate 17. When pedals begin to unfurl—Seafoam Yellow, Plate 31. When half bloom: inside of petals—White, Plate 53, with lower half of petal lightly overcast with Light Chalcedony Yellow, Plate 17; reverse of petals—White, Plate 53, with lower half of petal lightly overcast with Pale Dull Green-Yellow, Plate 17.
- *Sepals.*—Branched; curl back when petals begin to unfurl. Color: inside—Kildare Green, Plate 31; outside—Biscay Green, Plate 17.
- *Calyx.*—Color—Oil Green, Plate 5. Shape—Pear. Size — small. Aspect — smooth. Odor when rubbed—none.
- *Peduncle.* — Length — medium. Aspect — rough. Strength—erect; slender. Color—Lettuce Green, Plate 5.
- *Opening.*—Opens up well; is not affected by adverse weather conditions.

Bloom:
- *Size.*—Large; average size when fully expanded—4½ inches.
- *Borne.*—Singly and in irregular clusters.
- *Stems.*—Medium length; strong.
- *Form (when first open).*—Cupped. Permanence—Flattens.
- *Petalage.*—Double (full but open center). Number of petals under normal conditions—45.
- *Color.*—Center of flower—Seafoam Yellow, Plate 31. Outer petals—White, Plate 53. Base of petals (aiglet)—Marguerite Yellow, Plate 30. Inside of petals—White, Plate 53, with lower half of petal lightly overcast with Marguerite Yellow, Plate 30. Reverse of petals—White, Plate 53. General tonality from a distance—White, Plate 53.
- *Discoloration.*—General tonality at end of first day—White, Plate 53. Second day—White, Plate 53. Third day—White, Plate 53.

Petals:
- *Texture.*—Thin; is not affected by wet or hot weather.
- *Appearance.*—Inside—Satiny. Outside—Shiny.
- *Form.*—Oval.
- *Arrangement.*—Informal ("rags" in center).
- *Petaloids in center.*—Few; large.
- *Persistence.*—Drop off cleanly.
- *Fragrance.*—Moderate. Nature—Tea (average hybrid tea scent).
- *Last quality.*—On the plant—Long. As cut flower—Long.

GENITAL ORGANS

Stamens, anthers: Medium size; few; regularly arranged around styles. Color—Amber Brown, Plate 3.

Stamens, filaments (threads)—Medium length. Color—Naphthalene Yellow, Plate 16.

Pollen: Color—Cream Color, Plate 16.

Styles: Bunched; uneven length; short; thin.

Stigmas: Color—Ochraceous Buff, Plate 15.

Ovaries: All enclosed in calyx.

Hips: None.

Seeds: None.

PLANT

Form: Bush.

Growth: Vigorous; upright.

Foliage: 5 to 7 leaflets.
- *Size.*—Large.
- *Quantity.*—Normal.
- *Color.*—New foliage: Upper side—Oil Green, Plate 5, with serrations and veining of Oxblood Red, Plate 1; under side—Yellowish Oil Green, Plate 5, lightly overcast with Carmine, Plate 1. Old foliage: upper side—Forest Green, Plate 17; under side—Light Hellebore Green, Plate 17, lightly overcast with Garnet Brown, Plate 1.

*Shape.*—Oval pointed.

*Texture.*—Upper side—glossy. Under side—smooth.

*Ribs and veins.*—Ordinary.

*Edge.*—Serrated (saw-toothed).

*Serration.*—Both double and single; small.

*Leaf Stem.*—Color—Oil Green, Plate 5. Under side—prickles.

*Stipules.*—Medium length; bearded.

Wood:

*New Wood.*—Color—Oil Green, Plate 5. Bark—smooth.

*Old wood.*—Color—Forest Green, Plate 17. Bark—smooth.

Thorns:

*Thorns.*—Quantity: on main stalks from base— ordinary; on laterals from stalk—ordinary. Form—narrow base; short; hooked downward. Color (when young)—Carmine, Plate 1. Position—irregular.

*Prickles.*—Quantity: on main stalks—None; on laterals—none.

*Short needles.*—Quantity: on main stalks—none; on laterals—none.

I claim:

A new and distinct variety of rose plant of the large-flowered polyantha class, substantially as herein shown and described, characterized particularly as to novelty by its vigorous, free-growing and free-production habits of growth under normal greenhouse conditions, the attractive shape of its half-open buds and their suitability for cut flowers, the distinctive flat shape of its open flowers, with resulting hiding of the stamens, and the White color of its Floribunda type flowers.

No references cited.